(12) United States Patent
Ohmiya et al.

(10) Patent No.: US 8,367,357 B2
(45) Date of Patent: Feb. 5, 2013

(54) TWO SECRETORY LUCIFERASES

(75) Inventors: Yoshihiro Ohmiya, Ikeda (JP); Chun Wu, Ikeda (JP)

(73) Assignee: National Institute of Advanced Industrial Science and Technology, Tokyo-To (JP)

( * ) Notice: Subject to any disclaimer, the term of this patent is extended or adjusted under 35 U.S.C. 154(b) by 114 days.

(21) Appl. No.: 12/588,671

(22) Filed: Oct. 23, 2009

(65) Prior Publication Data

US 2011/0223610 A1    Sep. 15, 2011

Related U.S. Application Data

(62) Division of application No. 11/580,501, filed on Oct. 13, 2006, now abandoned.

(51) Int. Cl.
*C12Q 1/66* (2006.01)

(52) U.S. Cl. .......................................................... 435/8

(58) Field of Classification Search ........................ None
See application file for complete search history.

(56) References Cited

U.S. PATENT DOCUMENTS

| | | | | |
|---|---|---|---|---|
| 6,171,809 | B1 * | 1/2001 | Roelant | 435/8 |
| 6,228,604 | B1 * | 5/2001 | Escher et al. | 435/25 |
| 6,436,682 | B1 | 8/2002 | Bryan et al. | |
| 2008/0274485 | A1 | 11/2008 | Walia | |

FOREIGN PATENT DOCUMENTS

JP    2004-187652    7/2004

OTHER PUBLICATIONS

A.M. Chase et al. "*Cypridina* Luciferin Oxidation as a Function of pH, and Reduction of Luciferin by Ascorbic Acid", Johns Hopkins University, McCollum-Pratt Institute, Contribution No. 302: 258-61 (1961).*

A.K. Campbell et al. "Imidazolopyrazine Bioluminesence in Copepods and Other Marine Organisms" Marine Biology 104: 219-225 (1990).*

F.H. Johnson et al. "Action of Cyanide on *Cypridina* Luciferin", Journal of Cellular and Comparative Physiology, 59:265-272 (1962).*

Nakajima, Y. et al., "Multicolor luciferase assay system: one-step monitoring of multiple gene expressions with a single substrate," *BioTechniques*, 38(6): 891-894 (2005).

I. Bronstein et al., "Chemiluminescent and Bioluminescent Reporter Gene Assays", *Analytical Biochemistry* (1994), vol. 219, pp. 169-181.

Y. Nakajima et al., "eDNA Cloning and Characterization of a Secreted Luciferase from the Luminous Japanese Ostracod, *Cyprindina noctiluca*", Biosci. Biotechnol. Biochem. (2004), 68 (3), pp. 565-570.

J. Thompson et al., "Modulation of firefly luciferase stability and impact on studies of gene regulation", *Gene* (1991), 103: 171-177.

M. Verhaegan et al., "Recombinant Gaussia Luciferase. Oyerexpression, Purification, and Analytical Application of a Bioluminescent Reporter for DNA Hybridization", *Anal. Chem.* (2002), 74: 4378-4385.

B.A. Tannous et al., "Codon-Optimized Gaussia Luciferase cDNA for Mammalian Gene Expression in Culture and in Vivo", *Molecular Therapy* (2005), 11(3): 435-443.

* cited by examiner

*Primary Examiner* — Rebecca Prouty
(74) *Attorney, Agent, or Firm* — Wenderoth, Lind & Ponack, L.L.P.

(57) ABSTRACT

The present invention is one gene construct or a combination of two gene constructs or expression vectors incorporating a *Cypridina* luciferase gene and a copepod luciferase under the control of distinct promoters. These gene constructs and expression vectors are useful for making a mammalian cell incorporating the *Cypridina* luciferase gene and the copepod luciferase to be capable of stably expressed and extracellularly secreted under the control of the distinct promoters.

4 Claims, 9 Drawing Sheets

Fig. 3
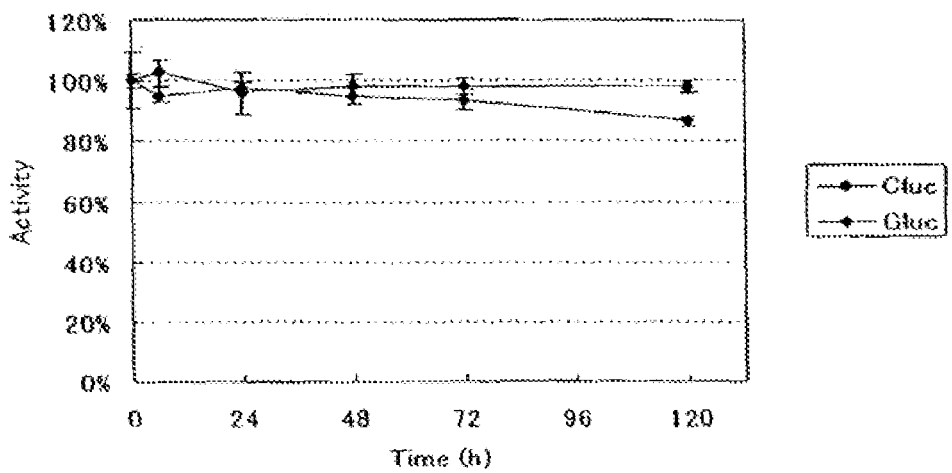
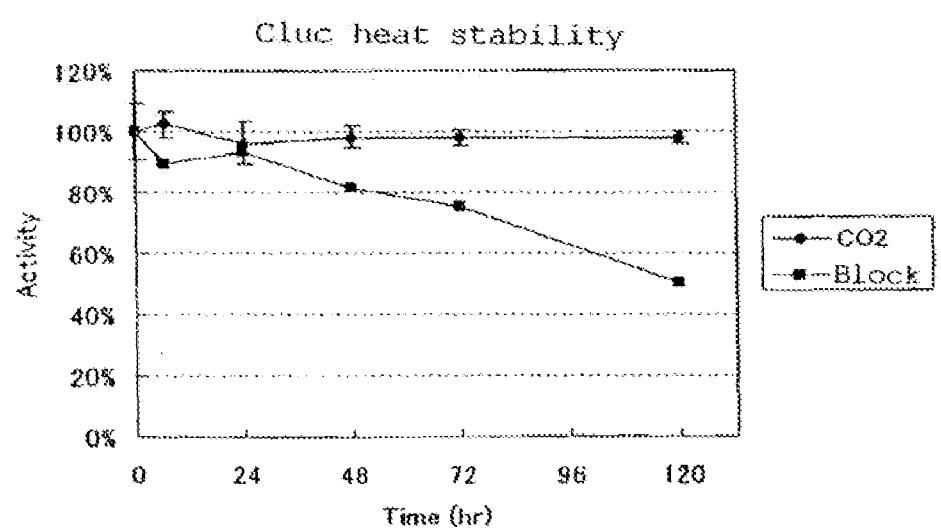
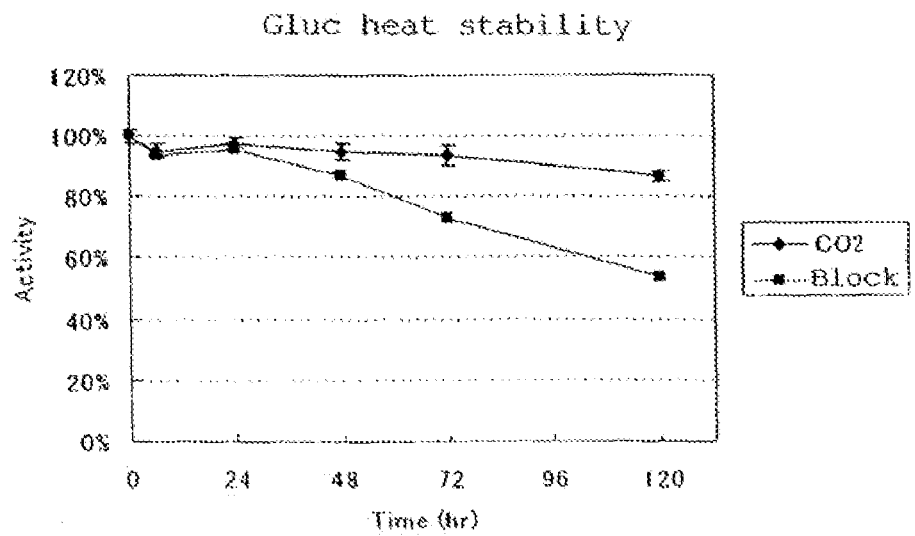

US 8,367,357 B2

TWO SECRETORY LUCIFERASES

This application is a Divisional of U.S. application Ser. No. 11/580,501, filed Oct. 13, 2006, now abandoned.

TECHNICAL FIELD

The present invention relates to luciferin and analogues thereof suitable for detecting multiple transcription activities of multiple genes in a cell in vivo with high throughput using secretory luciferases having different substrate specificity, constructs of secretory luciferase genes, expression vectors containing the constructs, transformed mammalian cells containing the constructs or the expression vectors, methods for screening drugs using the mammalian cells, and systems of measuring multiple transcription activities of respective promoters.

BACKGROUND ART

All events in vivo are caused directly or indirectly by changes of intracellular gene actions, and thus, it has been positioned as an important analysis method to measure an activity of gene transcription which occurs intracellularly in the field of life science. One of the analysis methods is referred to as a reporter assay, which is the method in which a reporter enzyme gene is inserted downstream of a gene sequence (gene transcription regulatory region) controlling a gene action, and an amount of a reporter enzyme which changes along with the change of the gene transcription regulatory region is evaluated by its enzyme activity, thereby evaluating the amount of gene transcription.

The most popular one as the reporter enzyme is firefly luciferase, and the transcription activity is evaluated by introducing a vector in which a firefly luciferase gene has been inserted downstream of the gene transcription regulatory region into cells and measuring an amount of luminescence which is the firefly luciferase enzyme activity expressed in the cells. In this measurement, when only one reporter enzyme is available, it is difficult to relatively evaluate a measured value because only one gene activity is measured. Thus, a dual reporter analysis by comparing with the value of transcription activity in the gene transcription regulatory region as the control has been developed, and a control reporter gene obtained by inserting an SV40 or CMV promoter sequence upstream of a *Renilla* luciferase gene taking a different luciferin (substrate) structure has been used. In this method, two gene transcription activities are evaluated by adding each luciferin to a cell lysate and measuring each amount of the luminescence, and the method has been commercialized by Promega. The other method in which expression amounts of three genes are evaluated in a multiple gene expression detection system similarly using firefly luciferin but using green, orange and red luciferases derived from beetles having different luminescent colors has been in practical use (Nakajima et al, Biotechniques, vol. 38, 891-894). In this method, three gene transcription activities are evaluated by adding firefly luciferin into the cell lysate and separating and quantifying mixed luminescence spectra, and the method has been commercialized by Toyobo.

In the reporter assay, the cells are stimulated for a certain time period, and the change of an expression amount of a particular gene is evaluated as an accumulated amount of the reporter enzyme in the cells. Thus, the accumulated amount is measured by lysing the cells which has passed over the certain time period. Therefore, it is impossible to measure with time using the same cell group or measure the same cell group again. In order to compensate this shortcoming, secretory luciferase has been noticed, and luciferases using *Cypridina* luciferase (JP 2004-187652-A) and copepod luciferase (*Gaussia* luciferase) (U.S. Pat. No. 6,436,682) (Prolume) have been in practical use. A secretory luciferase protein expressed by its gene is secreted extracellularly and accumulated in a culture medium. Thus, the expression amount of the gene is evaluated by collecting a part of the culture medium and adding a *Cypridina* luciferin or coelenterazine solution thereto to measure the enzyme activity of the reporter enzyme. When secretory luciferase is used, it is not necessary to lyse the cells. Thus, there is advantages in that the reporter assay can be performed using the alive cells and the assay with high throughput is possible by the use of a dispenser for a 96-well or 384-well plate. However, it is problematic in that the measured values can not be relatively evaluated because only one information is obtained.

Additionally, a background luminescence of coelenterazine is known to affect the luminescence of copepod luciferase (Anal. Chem. 2002, 74, 4378-4385).

DISCLOSURE OF INVENTION

The present invention aims at constructing and optimizing two reporter gene having secretory luciferase, which can measure or quantify multiple transcription activities in alive cells simultaneously or in the same time period, and further developing a dual gene transcription activity measurement system using the present reporter gene group to utilize for cell function analyses in life science, pathological treatments, examinations and drug discovery.

As a result of an extensive study for solving the above problems, the present inventor constructed a dual gene expression detection system using a *Cypridina* (including *Vargula*) luciferase gene and a copepod luciferase gene. In this system, the expression of two genes can be evaluated by inserting a different gene transcription regulatory region upstream of the *Cypridina* luciferase gene and the copepod luciferase gene, introducing the genes into cells by transfecting the cells simultaneously or sequentially, and measuring amounts of two enzymes accumulated in a culture medium after a certain time period. At that time, by dispensing parts of the culture medium from a 96-well or 384-well culture plate into two plates for measuring the luminescence, adding a *Cypridina* luciferin luminescence solution to one plate and a coelenterazine luminescence solution to another plate, and measuring continuously, it is possible to measure the transcription activities of two genes in many specimens in a short time period.

The present invention provides the following mammalian cell, gene construct, expression vector, method for screening drugs using the mammalian cell, kit and system for measuring each promoter transcription activity.

[1] One gene construct or a combination of two gene constructs incorporating a *Cypridina* luciferase gene and a copepod luciferase gene under the control of distinct promoters.

[2] One expression vector or a combination of two expression vectors incorporating a *Cypridina* luciferase gene and a copepod luciferase gene under the control of distinct promoters.

[3] A mammalian cell incorporating a *Cypridina* luciferase gene and a copepod luciferase gene to be capable of being stably expressed and extracellularly secreted under the control of distinct promoters.

[4] The mammalian cell according to [1] wherein one luciferase is under the control of the promoter subjected to evaluation and the other luciferase is under the control of the promoter subjected to comparison.

[5] A method for producing a mammalian cell incorporating a *Cypridina* luciferase gene and a copepod luciferase gene to be capable of being stably expressed and extracellularly secreted under the control of distinct promoters, characterized in that the gene construct or the combination thereof according to [1] or the expression vector or the combination thereof according to [2] is introduced into the mammalian cell.

[6] A kit for detecting dual gene expression of a *Cypridina* luciferase gene and a copepod luciferase gene incorporated into a mammalian cell, comprising *Cypridina* luciferin and coelenterazine.

[7] The kit according to [6] comprising a *Cypridina* luciferin solution and a coelenterazine solution.

[8] The kit according to [6] comprising the *Cypridina* luciferin solution containing *Cypridina* luciferin and at least one antioxidant and the coelenterazine solution containing coelenterazine and at least one antioxidant, wherein the antioxidant combined with the *Cypridina* luciferin is selected from the group consisting of ascorbic acid or salts thereof, erythorbic acid or salts thereof, or sulfite salts and the antioxidant combined with coelenterazine is selected from the group consisting of ascorbic acid or salts thereof, erythorbic acid or salts thereof, or sulfite salts.

[9] The kit according to [6] having a solution containing *Cypridina* luciferin and an ascorbate salt and a solution containing coelenterazine and an ascorbate salt.

[10] The kit according to [6] having a solution containing *Cypridina* luciferin, an ascorbate salt and a sulfite salt and a solution containing coelenterazine, an ascorbate salt and a sulfite salt.

[11] The kit according to [6] having a solution containing *Cypridina* luciferin, sodium ascorbate and sodium sulfite and a solution containing coelenterazine, sodium ascorbate and sodium sulfite.

[12] A method for screening drugs comprising a step of culturing the mammalian cell according to [3] in the presence of a drug candidate compound, a step of quantifying *Cypridina* luciferase and copepod luciferase extracellularly secreted in the presence or absence the candidate compound in the presence of *Cypridina* luciferin or coelenterazine, respectively, and a step of evaluating an effect of the candidate compound on a promoter subjected to evaluation ligated to at least one luciferase gene.

[13] A system of measuring multiple transcription activities of respective promoters ligated to respective luciferases before and after the change of a culture environment by changing the culture environment of the mammalian cell according to [3] and evaluating expression amounts of two luciferases.

According to the present invention, the reporter assay can be performed using the alive cells because the cells are not necessary to be lysed, and the assay with high throughput is possible by the use of the dispenser for the 96-well or 384-well plate.

In particularly preferable embodiments of the present invention, the method/system for simultaneously quantifying the transcription activities of two genes continuously with high throughput from luminescence activities of two luciferases secreted in the medium using *Cypridina* luciferase and copepod luciferase and using the alive cells is provided. By the use of this system, the multiple transcription assay in the cell can be measured simultaneously or almost simultaneously. These can be utilized for pathological treatments, examinations and drug discovery.

BRIEF DESCRIPTION OF THE DRAWINGS

FIG. 3 shows time stability of *Cypridina* luciferase and copepod luciferase in media;

BEST MODES FOR CARRYING OUT THE INVENTION

Figure 1:
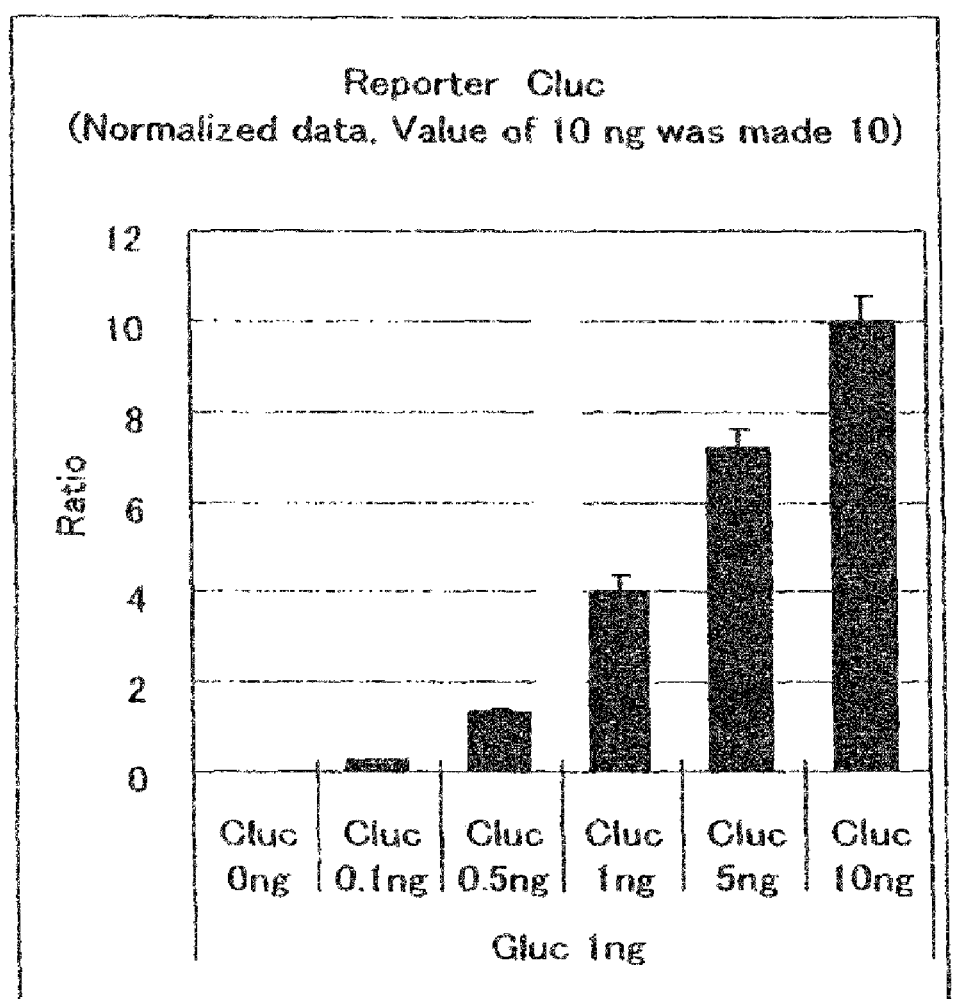
FIG. 1 shows the change of luminescence activity due to difference of gene amounts of *Cypridina* luciferase using a copepod luciferase gene as a control.

Herein, copepod luciferase is also referred to as an another name, *Gaussia* luciferase, and its base sequence and amino acid sequence are described in U.S. Pat. No. 6,436,682. Its closely related species include *Gaussia princeps* (AAG54095), *Pleuromamma* sp. CSG-2001 (AAG54096) and *Metridia longa* (AAR17541), and luciferases derived therefrom are included. Organisms from which *Cypridina* luciferase is derived include *Vargula hilgendorfii* (AAB86460) and its closely related species, e.g., *Cypridina noctiluca* (BAD08210), and synthetic DNA (BAD022610, BAE92278), and luciferases derived therefrom are included.

*Cypridina* luciferase may be naturally occurring *Cypridina* luciferase and may be derivatives thereof as described in PCT/JP2006/319000.

Coelenterazine may be naturally occurring coelenterazine and may be derivatives thereof as described in U.S. provisional application No. 60/833,105.

Both two luciferases used in the present invention are secretory, and its presence is easily detectable with fluorescence by adding each luciferin to the cell culture solution. When luminescence wavelengths of *Cypridina* luciferin and coelenterazine are close, the cell culture solution is divided into two and each luciferase can be separately detected by adding one of coelenterazine and *Cypridina* luciferin to one culture solution. Meanwhile when the combination in which the maximum luminescence wavelengths of *Cypridina* luciferin or the derivative thereof and coelenterazine or the derivative thereof differ by 40 nm or more, preferably 50 nm or more and particularly 60 nm or more, two luciferases can also be detected simultaneously by adding *Cypridina* luciferin or the derivative thereof and coelenterazine or the derivative thereof to one culture solution.

As the *Cypridina* luciferase gene and the copepod luciferase gene used in the present invention, the publicly known genes can be directly used. Alternatively, by (a) changing the cDNA sequence so that no additional transcription factor is bound, (b) changing codon usage (bias of use frequency of codons) to that for the mammals, and (c) changing the cDNA because many restriction enzyme sites limit the practical application in use, it is possible to more easily transcribe the *Cypridina* luciferase gene and the copepod luciferase gene in the mammalian cells.

In the conventional dual reporter assay, two luciferase accumulated in the cells were quantified using the cell lysate. Meanwhile, in the case of secretory luciferase, the ratio of the expression amounts of two luciferases was thought to easily change differently from intracellular luciferases because percentages of extracellularly secreted luciferase were different between luciferases and further extracellular and intracellular decompositions of luciferase were different. For example, the half life of firefly luciferase or *Renilla* luciferase which are the non-secretory luciferases conventionally used is about 3 hours (1. Thompson, J. F. et al. (1991) Gene 103, 171.) or about 5 hours (2. Bronstein, I. et al. (1994) Anal, Biochem. 219, 169). Meanwhile, the half life of secretory *Cypridina* luciferase is about 60 hours (Nakajima Y Biosci Biotechnol Biochem. 2004, 68, 565-70) and the half life of secretory copepod luciferase is about 24 hours or more (FIG. 3). This way, the half life is largely different between secretory luciferase and non-secretory luciferase.

When a ratio of the expression amounts of two luciferases in the dual reporter assay system is examined, it has been thought that the ratio several hours to 24 hours or 48 hours after being stimulated with a physiologically active substance and the like is largely different between secretory luciferase and non-secretory luciferase. However, the present inventor has found for the first time that the ratio of the expression amounts is kept nearly constant between luciferases and that almost the same results can be obtained in the conventional firefly luciferase/*Renilla* luciferase assay and in the *Cypridina luciferase*/copepod luciferase assay of the present invention.

In the present invention, the expression amounts of two enzymes after imparting the stimulation can be repeatedly quantified, suitable time periods after imparting the stimulation can be found for quantifying the expression amount of two luciferases, and thus, the assay can be performed for a short time as possible and is particularly useful for the assay with high throughput.

In preferable one embodiment of the present invention, it is desirable to increase the number of translation by stabilizing mRNA obtained by transcribing the *Cypridina* luciferase gene and the copepod luciferase gene. In this case, these genes can be sufficiently expressed in the mammalian cells by inserting a globulin intron to prolong a life span of mRNA and inserting Kozaks sequence to increase the number of translation.

Further technique in the preferable other embodiments of the present invention is, for example, to increase a copy number of mRNA, and thus, includes, for example, changing the codon usage (bias of use frequency of codons) to that for the mammals, changing the cDNA sequence so that no additional transcription factor is bound and changing the cDNA because many restriction enzyme sites limit the practical application in use. Such techniques are effective for the expression of two secretory luciferases in the mammalian cells. In particular, changing the codon usage (bias of use frequency of codons) to that for the mammals and changing the cDNA sequence so that no additional transcription factor is bound are effective.

The cDNA sequence can be changed in consideration of the following points in order of (1) to (4):

(1) It is better not to change the amino acid sequence of luciferase as possible.

(2) Subsequently, the cDNA sequence is changed so that an additional transcription factor is not bound.

(3) Further, the codon usage is changed to the codon usage for mammals in the cDNA sequence.

(4) If necessary, the cDNA sequence is changed to eliminate the restriction enzyme sites.

In one preferable embodiment, the gene construct of the present invention comprises a luciferase gene, a promoter upstream of the gene, if necessary an element which makes the translation more efficient and an element which stabilizes mRNA, and further can comprise an enhancer, SV40pA, a drug resistant gene (e.g., Neo').

In the present invention, mammals include human beings, cattle, horses, sheeps, monkeys, swines, mice, rats, hamsters, guinea pigs, rabbits and dogs, and are preferably the human beings.

The mammalian cell of the present invention which simultaneously express the *Cypridina* luciferase gene and the copepod luciferase gene can be obtained by making two gene constructs/expression vectors in which the *Cypridina* luciferase gene and the copepod luciferase gene have been incorporated under the control of distinct promoters and introducing these two gene constructs/expression vectors into the mammalian cell. Since the expression amount of each luciferase gene is proportion to the amount of the introduced gene constructs/expression vectors, an appropriate amount of the gene construct/expression vector for each gene is introduced into the mammalian cell. Generally, two luciferase genes are introduced into the mammalian cell so that the ratio of the expression amounts of the two genes is within 100 times, preferably 50 times and more preferably 30 times when measured upon no-stimulation and upon stimulation with a physiologically active substance such as a drug or an environmental factor. For the ratio of the amounts of the introduced two genes, considering the broadness of dynamic range, when the amount of the introduced one gene is 100, the amount of the introduced other gene is about 1 to 10,000 and preferably about 10 to 1,000. For the amounts of the introduced genes, those skilled in the art can optionally determine the preferable amounts in relation with strength of the promoter.

Alternatively, the transformed mammalian cell of the present invention can also be obtained by making one gene construct/expression vector in which the *Cypridina* luciferase gene and the copepod luciferase gene have been incorporated under the control of distinct promoters and introducing this into the mammalian cell. The ratio of the expression amounts of two genes can be make almost constant by incorporating two luciferase genes under the control of distinct promoters into one gene construct/expression vector.

The gene construct or the expression vector can be introduced into the mammalian cells using a gene introducing agent according to standard methods.

The kit for detection of dual gene expression of the present invention comprises *Cypridina* luciferin and coelenterazine, and if necessary further comprises buffer and an antioxidant for stabilizing the luciferin. *Cypridina* luciferin and coelenterazine may be contained as solids, but preferably is contained as solutions (particularly buffers) at certain concentrations in the kit. The buffer includes tris buffer, phosphate buffer, acetate buffer and Good buffer. A pH value of the buffer is about 5 to 9 and preferably about 6 to 8.

The pH value of the buffer for coelenterazine is about 5 to 9 and preferably about 7 to 8, and the pH value of the buffer for *Cypridina* luciferin is about 5 to 9 and preferably about 7 to 8.

The concentrations of *Cypridina* luciferin and coelenterazine in the solution is about 0.00001 to 0.1% by weight and preferably about 0.001 to 0.00001% by weight.

The antioxidant combined with *Cypridina* luciferin is at least one selected from the group consisting of ascorbic acid or salts thereof, erythorbic acid or salts thereof, or sulfite salts.

The antioxidant combined with coelenterazine is at least one selected from the group consisting of ascorbic acid or salts thereof, erythorbic acid or salts thereof, or sulfite salts.

The preferable antioxidant is at least one selected from ascorbic acid or salts thereof and sulfite salts, and particularly includes ascorbic acid or alkali metal salts thereof and alkali metal salts of sulfurous acid. The most preferable antioxidants are sodium ascorbate and sodium sulfite, and the combination thereof is particularly preferable. These antioxidants can increase the sensitivity by inhibiting the decomposition of *Cypridina* luciferin and coelenterazine to reduce the self-luminescence, inhibiting the increase of the background attributed to albumin such as BSA and HSA added in the system for stabilizing luciferase and reducing the S/N ratio.

Ascorbate salts, erythorbate salts and sulfite salts include alkali metal salts such as sodium, potassium and lithium salts, ammonium salts, and alkali earth metal salts such as calcium and magnesium salts.

When the antioxidant such as ascorbic acid is added to the biological luminescence system, if is preferable to add at a concentration of about 0.005 to 1M.

A composition comprising *Cypridina* luciferin and coelenterazine or a derivative thereof and the antioxidant is suitable for stabilizing coelenterazine or an analog thereof (solution, or solid such as powder, granule or crystal). The antioxidant is combined at 40000 to 800000 parts by weight relative to one part by weight of coelenterazine or the analog thereof in the composition.

Therefore, the composition comprising *Cypridina* luciferin and coelenterazine or the derivative thereof and the antioxidant (particularly, ascorbic acid and erythorbic acid and salts thereof) is particularly preferable because the composition not only can stably store *Cypridina* luciferin and coelenterazine or the derivative thereof at room temperature but also inhibit the increase of the background upon measurement.

To measure multiple specimens, the stability of luciferin is very important. Thus, it is particularly preferable to use a substrate solution in which 0.3 M of sodium ascorbate and 20 mM sodium sulfite which stabilize two luciferins have been added.

As the genes subjected to evaluation by the promoter and the control genes which are desirably determined simulataneously by the system of the present invention,
the genes subjected to evaluation include
clock genes (Per gene, Clock gene, BMAL gene, etc.)
oncogenes (cancer genes, tumor suppressing genes, mitosis marker genes, etc.)
disease-related genes (pathology-related genes, apoptosis genes, hormone genes, etc); and
the genes (control) subjected to comparison include
constitutively expressed genes (actin gene, GAPHD (glycelaldehyde-3-phosphate dehydrogenase) gene, SV40 viral gene derived from monkey, etc.).

In the assay system using dual luciferase genes of the present invention, both dual luciferase genes may be inserted under the control of the promoters of the different genes subjected to evaluation, and the ratio of the expression amounts of luciferases by the two promoters subjected to evaluation may be compared, or alternatively, one of two luciferase genes may be inserted under the control of the promoter of the gene subjected to evaluation and the other luciferase may be inserted under the control of the promoter of the gene subjected to comparison.

In the present invention, when one mammalian cell is constructed using the promoter A and the promoter B, another mammalian cell is constructed using the promoter A and the promoter C, and the promoter A is the promoter subjected to comparison (e.g., constitutively expressed promoter) and the promoters B and C are the promoter subjected to evaluation, then the ratio of the promoters B and C subjected to evaluation can also be evaluated by standardizing with the promoter A. Likewise, using three or more mammalian cells (the promoters subjected to evaluation incorporated in respective mammalian cells are different), the ratio of the expression amounts of luciferases by the three or more promoters subjected to evaluation can be standardized by the promoter subjected to comparison. This way, when two or more mammalian cells are combined, it is better that the ratio of luciferase genes are constant in each mammalian cell.

The present invention can be practically applied as follows.
(1) Primary Screening.

When it is supposed to exhaustively analyze multiple specimens, it is important to simultaneously obtain two or more information. Of course, multiple combinations are thought. In the case of the drug discover, to examine the drug efficacy, it is necessary to evaluate not only positive aspects but also negative aspects such as toxicity. Furthermore, the change of two genes at transcription level is reflected by a circumstance of the cell itself. Thus, it is preferable to use the constitutively expressed promoter which reflects the circumstance of the cell as the control. Therefore, the following combination is exemplified in drug discovery screening.

In tables 1 and 2, any of two luciferase may be ligated to the promoter.

TABLE 1

| Drug discovery screening | |
|---|---|
| Promoter subjected to evaluation | Evaluation of drug efficacy |
| Toxicity evaluation promoter (apoptosis-related) or constitutively expressed promoter | Evaluation of drug safety or cell state |

In this case, the toxicity evaluation or the constitutive expression is the control for the promoter of the gene subjected to evaluation as the drug.

In the case of evaluating the relation of three promoters, the mammalian cell (promoter subjected to evaluation+constitutively expressed promoter) which standardizes the drug efficacy could be combined with the mammalian cell (toxicity evaluation promoter+constitutively expressed promoter) which standardizes the safety.

TABLE 2

| Search of target promoter sequence | |
|---|---|
| Unspecified promoter (sequence group with unknown effect on promoter library | Evaluation of drug efficacy |
| Pseudo-promoter sequence (random sequence or meaningless sequence) | Evaluation of drug safety |
| Constitutively expressed promoter | Evaluation of cell state |

In this case, the pseudo-promoter and the constitutively expressed promoter are the control for the promoter subjected to screening.

In the case of evaluating the relation of three promoters, the mammalian cell (unspecified promoter+constitutively expressed promoter) which standardizes the promoter effect could be combined with the mammalian cell (pseudo-promoter sequence+constitutively expressed promoter) which standardizes pseudo-information.

Meanwhile, in the combination of four promoters, there is an advantage that an external factor such as environmental hormone can be simultaneously evaluated, and it is possible to determine the change of the transcription activity of multiple genes in the cell affected by the external factor. For example, the expression of the receptor which directly captures the external factor can be monitored.

TABLE 3

| Unspecified promoter (sequence group with unknown effect on promoter library) | Evaluation of external factor effect |
|---|---|
| Pseudo-promoter sequence (random sequence or meaningless sequence) | Evaluation of external factor safety |
| Promoter sequence of receptor protein of external factor | Evaluation of receiving process of external factor |
| Constitutively expressed promoter | Evaluation of cell state |

In this case, the protein receiving the external factor, the protein directly affected by it, and further the safety of the cell itself can be evaluated, and the information given to the cell by the external factor can be correctly evaluated by standardizing these by the control of the protein of the constitutively expressed promoter.

In the case of determining the relation of four promoters, for example, the mammalian cell (unspecified promoter+constitutively expressed promoter) which standardizes the promoter effect, the mammalian cell (pseudo-promoter sequence+constitutively expressed promoter) which standardizes the pseudo-information and the mammalian cell (promoter of receptor protein of external factor+constitutively expressed promoter) which standardizes external factor reception could be combined.

(2) Secondary Screening

When it is supposed to evaluate the efficacy of the focused drug or the promoter information and obtain, it is important to obtain three or more information. In the drug discovery, multiple drug efficacies are often supposed. First, it is important to know the gene expressing the change of the cell state and the temporary effect (e.g., toxicity, shock response, etc.) of the drug, and to also know the actual effect. For example, an evaluation system of a clock-related drug efficacy as shown in Table 4 can be exemplified.

TABLE 4

| Evaluation system of clock-related drug efficacy | |
|---|---|
| Drug appreciation promoter (e.g., toxicity, shock response, etc.) | Evaluation of temporary drug efficacy |
| Circadian rhythm promoter (sequence of BMAL or per gene) | Evaluation of biological clock |
| Drug responsive promoter | Evaluation of intracellular drug efficacy |

In the case of determining the relation of three promoters, for example, the mammalian cell (Drug responsive promoter+Drug appreciation promoter) which standardizes the temporary and sustained drug efficacies could be combined with the mammalian cell (Drug responsive promoter+Circadian rhythm promoter) which standardizes the relation of the drug and the circadian rhythm.

In the present invention, the assay can be performed with high throughput, and after the same stimulation, two luminescences can be measured and evaluated nearly simultaneously in many cell types and alive cells. Thus, the present invention is particularly useful for evaluating the drug efficacy according to a clock axis.

The drug efficacy on the combination of multiple manipulations (history) can be evaluated by performing a series of the manipulations for the same cell.

*Cypridina* luciferase and copepod luciferase used in the present invention are gradually decomposed in air after being secreted out of the mammalian cells. Thus, it is desirable to culture the mammalian cells under the condition where the contact with the air is prevented, for example, in a $CO_2$ incubator. Until after 72 hours, the ratio of the expression amounts of the secretory luciferases can be measured with high accuracy. In the case of culturing under the condition, e.g., in a heat block where the luciferase is likely to contact with the air, it is preferable to measure the expression amounts of luciferases in a short time as possible, e.g., within 24 hours after the stimulation.

EXAMPLES

The present invention will be described in more detail using the following Examples, but it goes without saying that the present invention is not limited to these Examples Example 1

A vector pcDNA3-CL in which a *Cypridina* luciferase gene had been inserted into pcDNA3 supplied from Invitrogen and a copepod luciferase gene pCMV-Gluc were made. NIN3T3 cells were seeded at $3 \times 10^4$ per well in a 48-well plate and cultured for one day. Subsequently, the plasmid pcDNA3-CL which was a reporter gene at 0, 0.1, 0.5, 1, 5 and 10 ng/well or the plasmid pCMV-Gluc which was an internal control gene at 1 ng/well was added so that a total plasmid amount was adjusted to 100 ng/well by adding pcDNA3. Then, using a Lipofectamine Plus reagent, the transfection was performed. The cells were cultured in DMEM containing 10% FBS for two days, and then the medium was collected. Subsequently, 50 μL of 1 μM *Cypridina* luciferin (0.06 M phosphoric acid (pH 6.4), 0.3 M sodium ascorbate, 20 mM sodium sulfite) or 1 μM coelenterazine (0.06 M phosphoric acid (pH 6.4), 0.3 M sodium ascorbate, 20 mM sodium sulfite) was added to 5 μL of the collected medium using an injector, and an integrated value for 10 seconds was measured using AB2100-JNR.

As a result, the activity in the plasmid of copepod luciferase as the internal control was almost the same level, while the activity in the plasmid of *Cypridina* luciferase was linearly increased depending on the amounts of the transfected plasmid pcDNA3-CL (FIG. 1). This demonstrated that two luciferase having the different substrate specificity were not interfered one another and that the luminescence amount is well-correlated to the vector amount.

Example 2

The vector pcDNA3-CL (Biosci Biotechnol Biochem. 2004 March; 68(3):565-70. cDNA cloning and characterization of a secreted luciferase from the luminous Japanese ostracod, *Cypridina* noctiluca. Nakajima Y, Kobayashi K, Yamagishi K, Enomoto T, Ohmiya Y) in which the *Cypridina* luciferase gene had been inserted into pcDNA3 supplied from Invitrogen and an expression vector pCMV-Gluc (supplied from New England BioLabs) containing the copepod luciferase gene were made. NIN3T3 cells were seeded at $3\times10^4$ per well in a 48-well plate and cultured for one day. Subsequently, the plasmid pCMV-Gluc which was the reporter gene at 0, 0.1, 0.5, 1, 5 and 10 ng/well or the plasmid pcDNA3-CL which was the internal control gene at 1 ng/well was added so that the total plasmid DNA amount was adjusted to 100 ng/well by adding pcDNA3. Then, using the Lipofectamine Plus reagent, the transfection was performed. The cells were cultured in DMEM containing 10% FBS for two days, and then the medium was collected. Subsequently, 50 μL of 1 μM *Cypridina* luciferin (0.06 M phosphoric acid (pH 6.4), 0.3 M sodium ascorbate, 20 mM sodium sulfite) or 1 μM coelenterazine (0.06 M phosphoric acid (pH 6.4), 0.3 M sodium ascorbate, 20 mM sodium sulfite) was added to 5 of the collected medium using the injector, and the integrated value for 10 seconds was measured using AB2100-JNR.

Figure 2:
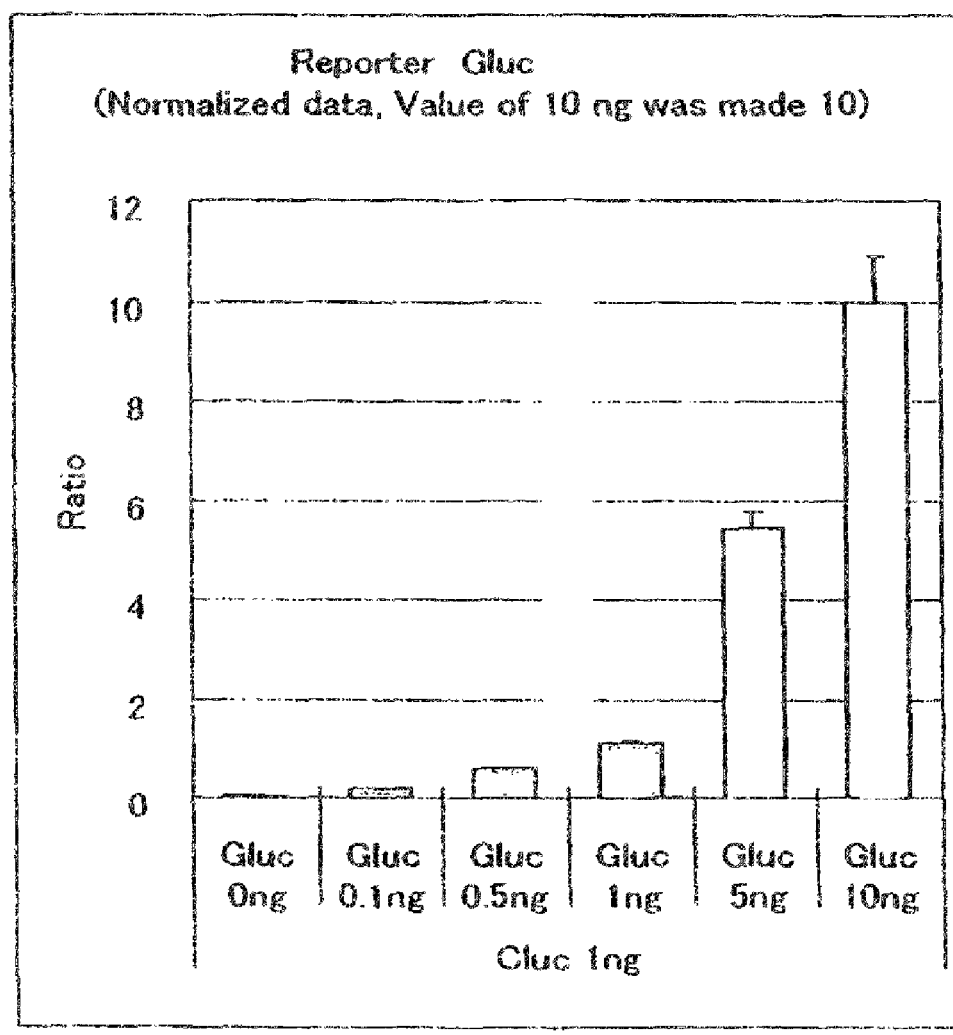
FIG. 2 shows the change of luminescence activity due to difference of gene amounts of copepod luciferase using a *Cypridina* luciferase gene as a control.

As a result, the activity in the plasmid of *Cypridina* luciferase as the internal control was almost the same level, while the activity in the plasmid of copepod luciferase was linearly increased depending on the amounts of the transfected plasmid pCMV-Gluc (FIG. 2). This demonstrated that two luciferase having the different substrate specificity were not interfered one another and that the luminescence amount is well-correlated to the vector amount.

From FIGS. 1 and 2, it was shown that when any of *Cypridina* luciferase and copepod luciferase was used as the control gene, the similar results were obtained.

Example 3

The stability of *Cypridina* luciferase and copepod luciferase at 37° C. was examined in the $CO_2$ incubator. NIN3T3 cells were seeded in a 24-well plate, cultured for one day, and then transfected with 100 ng of pcDNA3-CL and 100 ng of pCMV-Gluc. The cells were cultured in 10% FBS+DMEM for one day, the medium was collected, and diluted 10 times with 10% FBS+DMEM to prepare a Cluc and Gluc mixture solution. Subsequently, 55 μL of the Cluc and Gluc mixture solution was dispensed in a 96-well plate, and collected at 0, 6, 24, 48, 72 and 120 hours. Then 50 μL of the luciferin solution was added to 50 μL of a sample, and the integrated value for 10 seconds was measured using JNR. In all experiment, n is 4. As a result, it was demonstrated that both luciferases had 95% or more activity until about 72 hours, the activity of copepod luciferase was reduced to about 80% after 120 hours had passed and two luciferase did not exhibit relatively the same relation (FIG. 3A). Meanwhile, it was shown that the relative relation of the luminescence activity was constant until about 72 hours. But, as shown in FIGS. 3B and 3C, both *Cypridina* luciferase and copepod luciferase activities were largely reduced on the heat block on which the enzymes were likely to contact with the air whereas the activities in the $CO_2$ incubator were not reduced. Therefore, in order to keep the relative relation of the luminescence activity constant until about 72 hours, it is desirable to keep the culture state in the $CO_2$ incubator. When cultured on the heat block, it is preferable to measure until after 24 hours.

Example 4

Figure 4:
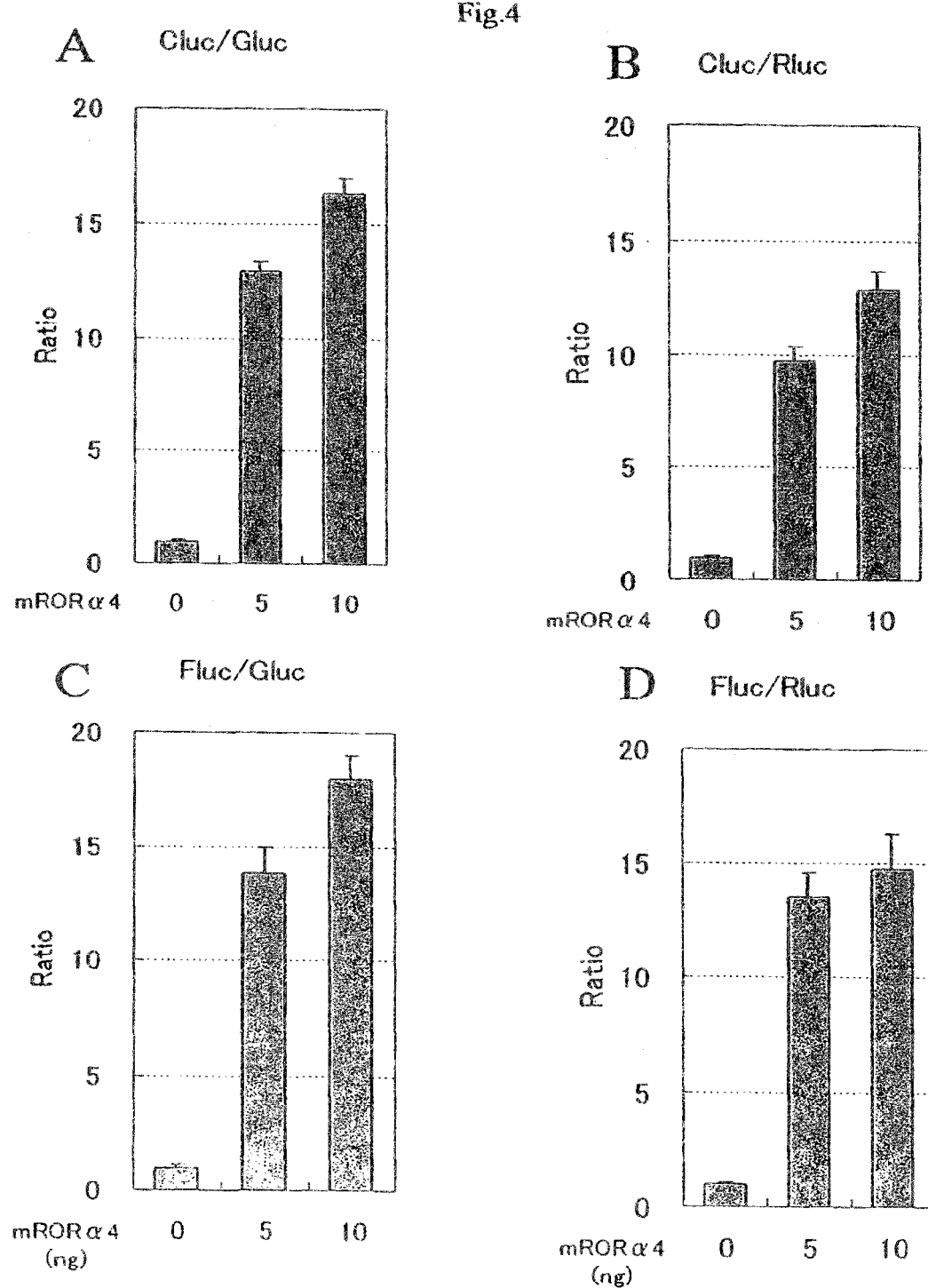
FIG. 4 shows results of dual reporter assay of Bmal1 promoter (*Cypridina* luciferase) (using *Renilla* luciferase and copepod luciferase as the controls)

A vector pBMAL1-CL-IRES-FL in which *Cypridina* luciferase had been inserted downstream of the promoter sequence of the clock gene BMAL1 and further firefly luciferase had been inserted further downstream thereof subsequent to an IRES sequence was constructed (Yamagishi K, Enomoto T, Ohmiya Y, Analytical Biochemistry (2006) 354, 15-21). NIH3T3 cells were seeded in a 24-well plate at $4\times10^4$ per well, and cultured for one day. Subsequently, pBMAL1-CL-IRES-FL at 50 ng/well, pCR3.1-RORα4 for the expression of the transcription factor at 0, 5 or 50 ng/well and copepod luciferase pCMV-Gluc at 1 ng/well were added to the wells so that the total plasmid DNA amount was adjusted to 105 ng/well by adding pBluescript plasmid, and the cells were transfected using Lipofectamine Plus reagent. As the control, the cells were transfected with phRL-TK at 5 ng/well. After the transfection, the cells were cultured in DMEM containing 10% FBS for one day, and then the medium collected. To 50 μL of the collected medium, 50 μL of 1 μM *Cypridina* luciferin (0.06 M phosphoric acid (pH 6.4), 0.3 M sodium ascorbate, 20 mM sodium sulfite) for Cluc activity, 50 μL of 1 μM coelenterazine (0.06 M phosphoric acid (pH 6.4), 0.3 M sodium ascorbate, 20 mM sodium sulfite) for Gluc activity and Rluc activity, or Pikkagene luminescence reagent II for Fluc activity was added using the injector, and the integrated value for 10 seconds was measured using AB2100-JNR (FIG. 4) In all experiments, n is 4. As a result, the transcription activity of the BMAL1 promoter was activated by its transcription factor, RORα4, and the activity of *Cypridina* luciferase was linearly increased. When *Renilla* luciferase conventionally used as the control vector was compared with the novel copepod luciferase, they showed the similar tendency. When *Renilla* luciferase was used, it was necessary to lyse the cells, but when copepod luciferase was used, the measurement could be performed without lysing the cells and the relative evaluation became possible.

Example 5

Figure 5:
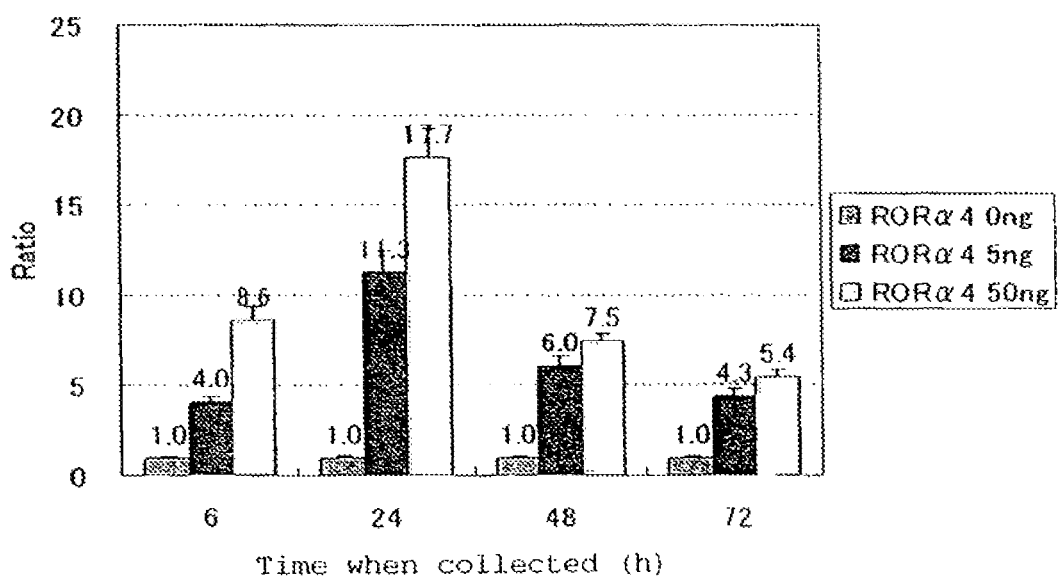
FIG. 5 shows the results of time course assay in the dual reporter assay of Bmal1 promoter (using copepod luciferase as the control)

As the dual reporter assay of Bmal1 promoter, NIH3T3 cells were seeded in a 24-well plate at $5\times10^4$ per well, and cultured for one day. Subsequently, the reporter pBMAL1-CL-IRES-FL at 50 ng/well, pCR3.1-RORα4 for the expression of the transcription factor at 0, 5 or 50 ng/well and the internal control pCMV-GL at 5 ng/well were added to the wells so that the total plasmid DNA amount was adjusted to 105 ng/well by adding pBluescript plasmid, and transfected the cells. The cells were cultured in 500 μL of DMEM containing 10% FBS, and 220 μL of the medium was collected at 6, 24, 48 and 72 hours. Upon collecting the sample, 220 μL of the new medium was added, and the collection was continued. To 50 of the sample collected at each time, 50 W, of 1 μM *Cypridina* luciferin (0.06 M phosphoric acid (pH 6.4), 0.3 M sodium ascorbate, 20 mM sodium sulfite) for the Cluc activity or 50 μL of 1 μM coelenterazine (0.06 M phosphoric acid (pH 6.4), 0.3 M sodium ascorbate, 20 mM sodium sulfite) for the Gluc activity and Rluc activity was added using the injector, and the integrated value for 10 seconds was measured using JNR (FIG. 5) In all experiments, n is 4. As a result, the transcription activity of the BMAL1 promoter was activated by its transcription factor, ROR(4, and the activity of *Cypridina* luciferase was linearly increased every collection time compared with copepod luciferase used as the control vector. The transcription activity was changed in the collection time, maximized at 24 hours, and was the similar level at 6, 48 and 72 hours. But, the difference was observed in the relative relation of the transcription activity between 5 ng and 10 ng of pCR3.1-ROR(4 for the transcription factor expression. Conventionally, only the relation of relative gene expressions in the same cell at a certain time was obtained, but by the use of the present invention, it was shown to be capable of analyzing the change of the gene expressions in the same cell at a certain time and with time.

Example 6

Figure 6:
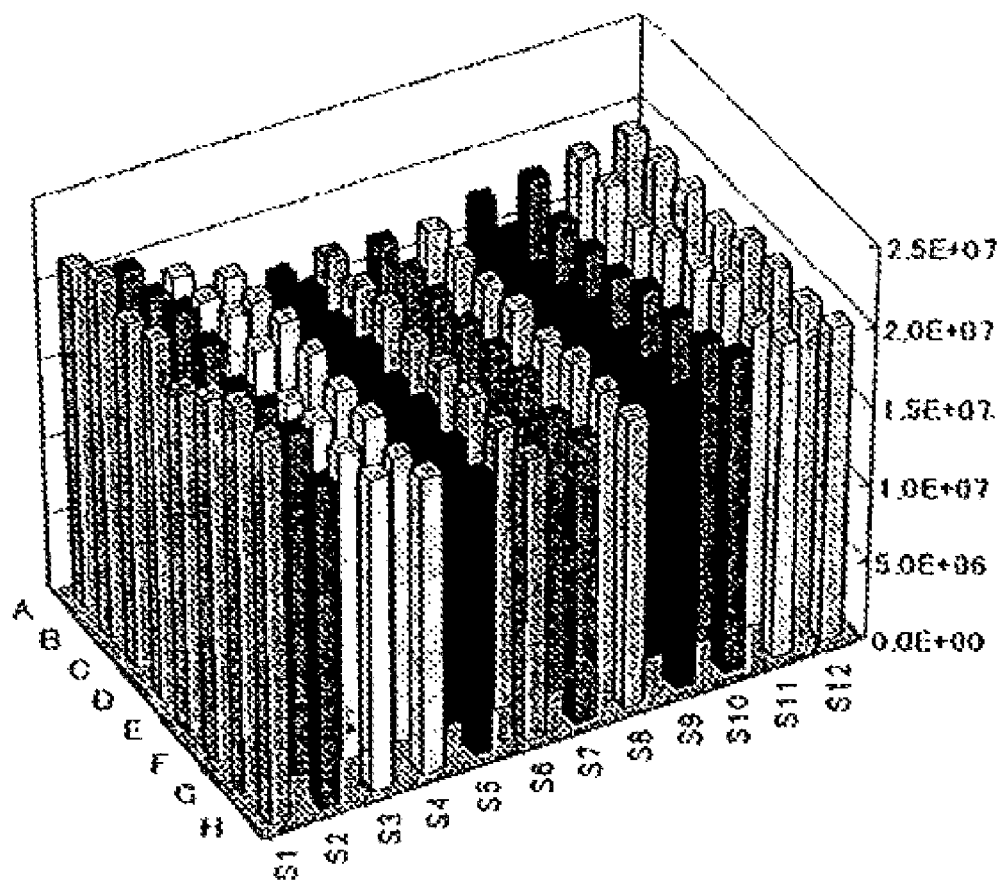
FIG. 6 shows the results of measuring the luminescence activity of *Cypridina* luciferase in a 96-well plate.

The possibility of the analysis with high throughput to analyze many specimens was confirmed. NIN3T3 cells were co-transfected with pcDNA3-CL and pCMV-Gluc at 10 ng/well, and after 24 hours, the culture medium was collected. The medium was diluted 10 times with the new DMEM containing 10% FBS to prepare a Cluc and Gluc mixture solution, and 50 μL thereof was dispensed in a 96-well plate and measured. FIG. 6 shows the result of measuring by adding 1 μM *Cypridina* luciferin (0.06 M phosphoric acid (pH 6.4), 0.3 M sodium ascorbate, 20 mM sodium sulfite) to the 96-well plate for luminescence measurement dispensed from the 96-well cell culture plate. When *Cypridina* luciferase was used, a characteristic of variation CV was 8.4%. The characteristic of variation CV when copepod luciferase was used was 9.1 although the figure is not shown. For both enzymes, it was demonstrated that even when dispensed in the 96-well plate, the stable data could be obtained, indicating that the dual reporter assay with high throughput was possible.

Example 7

Figure 7:
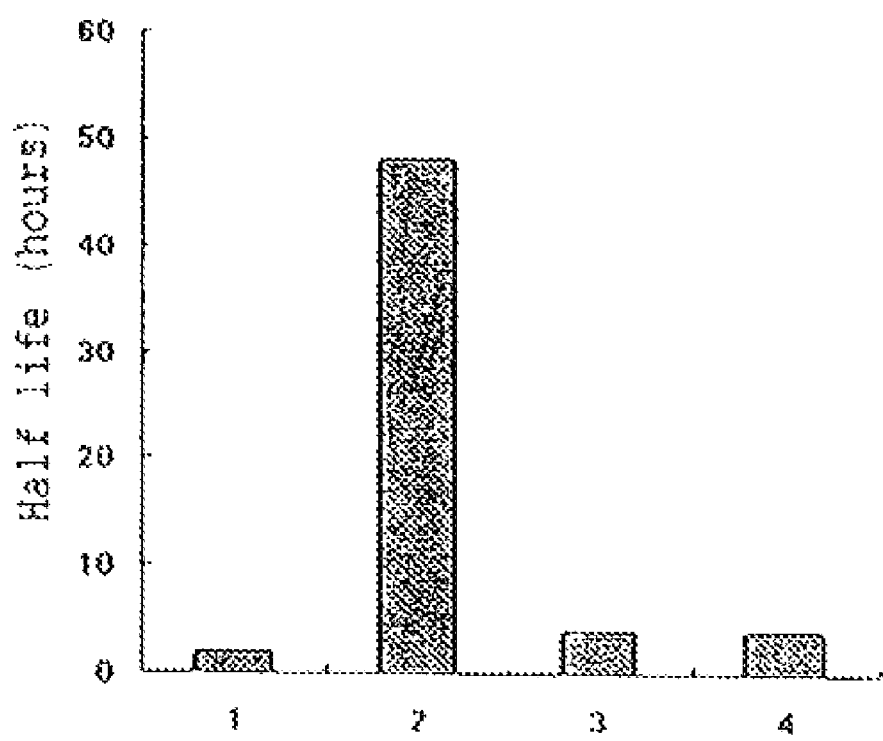
FIG. 7 shows a half life of coelenterazine in the presence or absence of an antioxidant.

The following four solutions were prepared, coelenterazine was dissolved at a final concentration of 10 μM, and the residual activity of coelenterazine was examined to determine a halflife. The result is shown in FIG. 7. In FIG. 7, the halflife is shown in the solution of (1) 0.1M Tris-HCl pH 7.4/0.3 M NaCl, (2) 0.1M Tris-HCl pH 7.4/0.3 M Sodium ascorbate, (3) 0.1M Tris-HCl pH 7.4/0.2 M Na$_2$SO$_3$ or (4) 0.1M Tris-HCl pH 7.4/0.2 M Thiourea. As shown in FIG. 7, the half life was widely prolonged in the sodium ascorbate solution. It is desirable to add sodium ascorbate in the dual reporter assay.

Example 8

Self-Luminescence Activity of Coelenterazine in 10% FBS Solution

Figure 8:
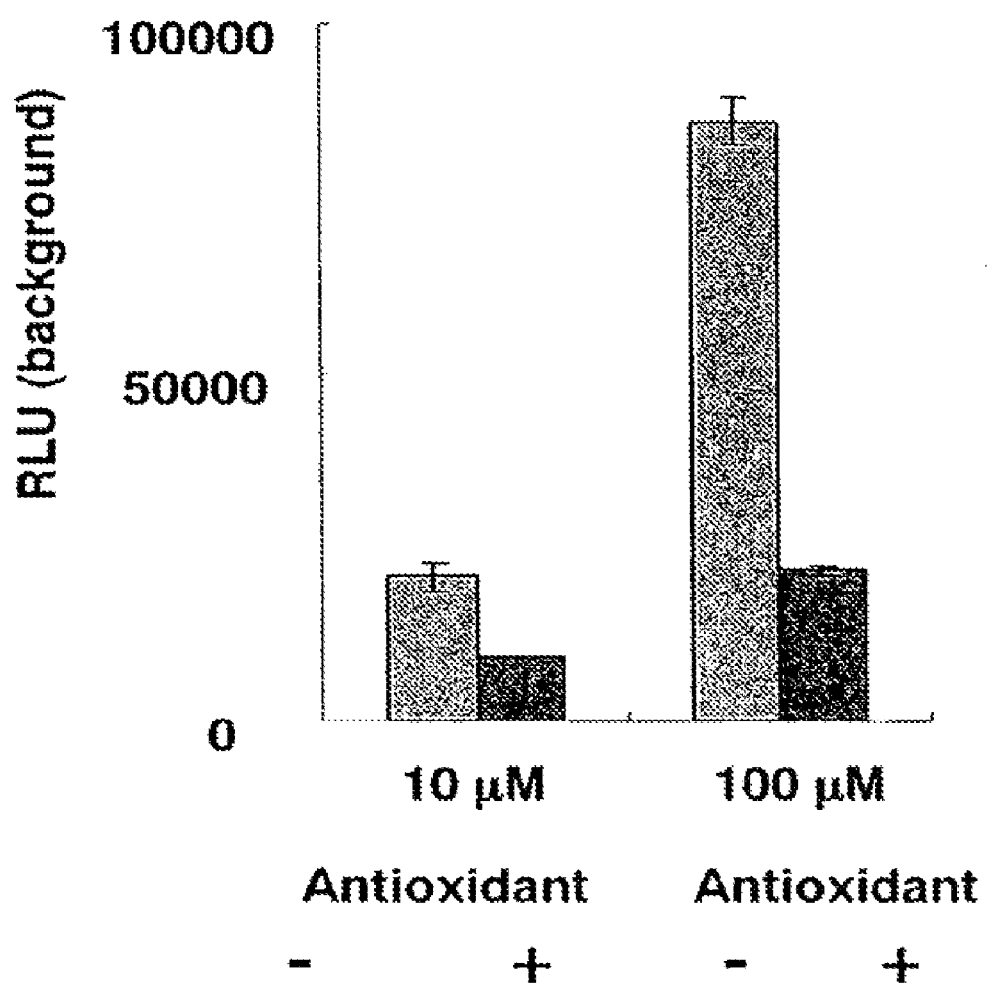
FIG. 8 shows self-luminescence of coelenterazine in a 10% FBS solution.

The following two solutions were prepared, coelenterazine was dissolved at a final concentration of 10 μM or 100 μM, the solution was mixed with the medium for animal cells (solution containing 10% FBS), and the luminescence for 10 seconds was measured as the background. At that time, a reaction solution was 0.1M Tris-HCl pH 7.4/0.3 M, and the effect with or without the addition of 0.3 M sodium acetate was examined. The luminescence activity (RLU: relative light unit) was measured, the ratio of its actually measured value to the self-luminescence was calculated and correctively shown in FIG. 8. As a result, the reduction of the self-luminescence could be accomplished by adding the sodium ascorbate salt solution.

Example 9

Ratio of Luminescence to Self-Luminescence by Copepod Luciferase

Figure 9:
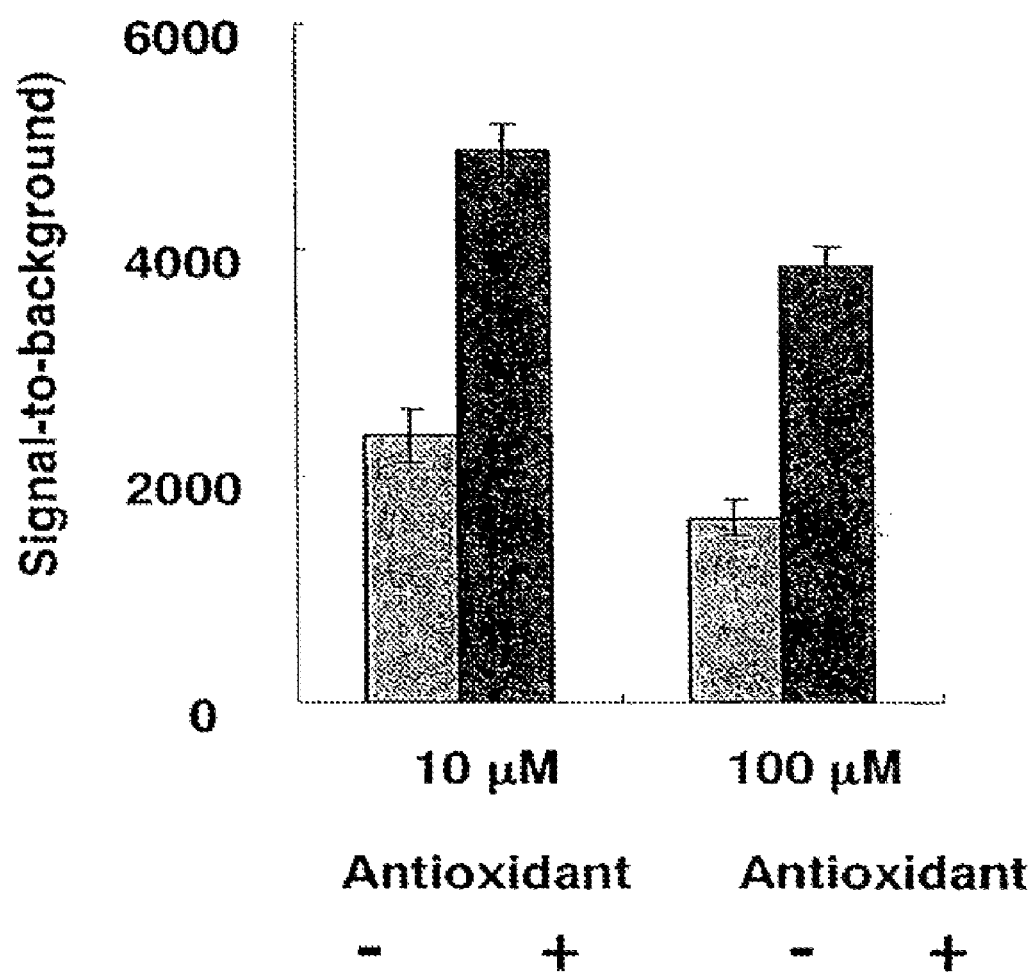
FIG. 9 shows a ratio of luminescence by copepod luciferase to self-luminescence.

Using the medium (containing 10% FBS) of copepod luciferase secreted from the animal cells, the coelenterazine solution prepared in Example 8 was dissolved at a final concentration of 10 μM or 100 μM, and the resulting solution was mixed with the medium (containing 10% FBS) for the animal cells at 1:1 (volume ratio), and the luminescence for 10 seconds was measured as the background activity. At that time, a reaction solution was 0.1M Tris-HCl pH 7.4/0.3 M, and the effect with or without the addition of 0.3 M sodium acetate was examined. The luminescence activity was measured, the ratio of the actually measured value to the self-luminescence (signal to background) was calculated, and collectively shown in FIG. 9. As a result, the sodium ascorbate salt solution improved the ratio of the luminescence to the self-luminescence at least two times or more. This way, the antioxidant has almost no effect on the oxidation reaction by luciferase and could reduce only the background.

The invention claimed is:

1. A kit for detecting dual gene expression of a *Cypridina* luciferase gene and a copepod luciferase gene incorporated into a mammalian cell, comprising:
   a *Cypridina* luciferin solution containing *Cypridina* luciferin, an ascorbate salt and a sulfite salt, and
   a coelenterazine solution containing coelenterazine and at least one antioxidant, wherein the antioxidant is selected from the group consisting of ascorbic acid, an ascorbic acid salt, erythorbic acid and an erythorbic acid salt.

2. The kit according to claim 1, comprising a solution containing coelenterazine and an ascorbate salt.

3. The kit according to claim 1, comprising a solution containing coelenterazine, an ascorbate salt and a sulfite salt.

4. The kit according to claim 1, comprising a solution containing *Cypridina* luciferin, sodium ascorbate and sodium sulfite, and a solution containing coelenterazine, sodium ascorbate and sodium sulfite.

* * * * *